United States Patent
Jeschke et al.

(10) Patent No.: US 6,291,492 B1
(45) Date of Patent: *Sep. 18, 2001

(54) 3-ARYL ALKENYL-1,2,4-OXADIAZOLE DERIVATIVES AND THEIR USE AS PARASITICIDES FOR ANIMALS

(75) Inventors: Peter Jeschke, Leverkusen; Ulrike Wachendorff-Neumann, Neuwied; Christoph Erdelen, Leichlingen; Norbert Mencke, Leverkusen; Andreas Turberg, Erkrath, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/669,480

(22) PCT Filed: Jan. 4, 1995

(86) PCT No.: PCT/EP95/00025

§ 371 Date: Jul. 11, 1996

§ 102(e) Date: Jul. 11, 1996

(87) PCT Pub. No.: WO95/19354

PCT Pub. Date: Jul. 20, 1995

(30) Foreign Application Priority Data

Jan. 17, 1994 (DE) .................................................. 44 01 107

(51) Int. Cl.$^7$ .......................... A01N 43/82; C07D 271/06

(52) U.S. Cl. ............................................. 514/364; 548/131
(58) Field of Search ............................... 548/131; 514/364

(56) References Cited

U.S. PATENT DOCUMENTS 5,428,049 * 6/1995 Jeschke ................................. 514/364

* cited by examiner

*Primary Examiner*—Robert Gerstl
(74) *Attorney, Agent, or Firm*—Norris McLaughlin & Marcus

(57) ABSTRACT

The invention relates to new 3-aryl-alkenyl-1,2,4 - oxadiazole derivatives of the formula (I)

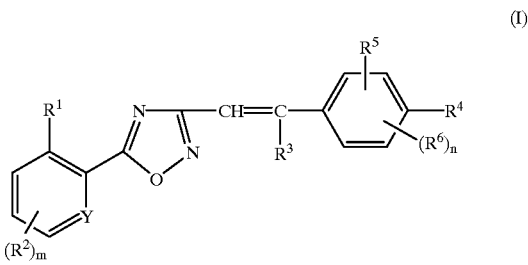

in which
$R^1$, $R^2$, $R^3$, $R^4$, $R^5$, $R^6$, Y, m and n have the meanings given in the description,
to a plurality of processes for their preparation, and to their use as pesticides.

8 Claims, No Drawings

3-ARYL ALKENYL-1,2,4-OXADIAZOLE DERIVATIVES AND THEIR USE AS PARASITICIDES FOR ANIMALS

The invention relates to new 3-aryl-alkenyl-1,2,4-oxadiazole derivatives, to a plurality of processes for their preparation, and to their use for combating animal pests.

The preparation of a variety of 3,5-disubstituted 1,2,4-oxadiazoles such as, for example, 5-(2,4-dichlorophenyl)-3-[2-(2,4-dichlorophenyl)-ethenyl]-1,2,4-oxadiazole, has already been described (cf. J. Heterocycl. Chem., 15 (8), 1373–8, 1978).

Equally, it is already known that certain 1,2,4-oxadiazole derivatives have a parasiticidal (in particular endoparaciticidal) activity in humans and animals (cf. U.S. Pat. No. 4,012,377 and German Offenlegungschrift 40 41 474).

Furthermore, it is known that certain 1,2,4-oxadiazole derivatives can be used as insecticides and acaricides (cf. DE 41 24 151).

However, the activity of these prior-art compounds is not always entirely satisfactory in all fields of application, in particular when low amounts and concentrations are applied.

There have now been found new 3-aryl-alkenyl-1,2,4-oxadiazole derivatives of the formula (I)

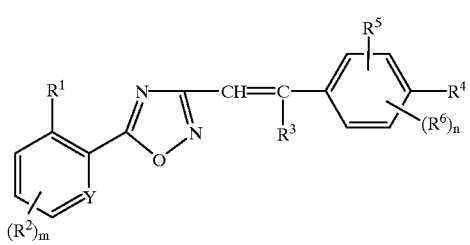

(I)

in which
  $R^1$ represents halogen, alkyl or alkoxy,
  $R^2$ represents hydrogen, halogen, halogenoalkyl or halogenoalkoxy,
  $R^3$ represents hydrogen or alkyl,
  $R^4$ represents halogen, trialkylsilylalkyl, trialkylsilylalkoxy; or a group $-A_k-R^7$, in which
    A represents oxygen, sulfur, SO, $SO_2$, alkylene, alkyleneoxy, alkylenethio, oxyalkylene, oxyalkyleneoxy, alkyleneoxyalkylene, alkenediyl or alkinediyl,
    k represents a number 0 or 1,
    $R^7$ represents alkyl, halogenoalkyl, alkenyl, halogenoalkenyl, alkinyl or halogenoalkinyl, optionally substituted cycloalkyl, optionally substituted phenyl or optionally substituted pyridyl, or
  $R^4$ represents optionally substituted cycloalkyl, where, if appropriate, one or two $CH_2$ groups which are not linked directly to each other are replaced by oxygen and/or sulfur,
  $R^5$ and $R^6$ represent hydrogen, halogen, alkyl, halogenoalkyl, alkoxy or halogenoalkoxy,
  m represents a number 1, 2 or 3,
  n represents a number 1 or 2,
  Y represents a nitrogen atom or the group $C-R^9$ in which
    $R^9$ represents hydrogen, halogen or alkyl;
with the exception of the compounds:
  5-(2,4-dichlorophenyl)-3-[2-(2,4-dichlorophenyl)-ethenyl]-1,2,4-oxadiazole (cf. J. Heterorcycl. Chem. 15 (8), 1373—8, 1978) and 5-(2,6-difluorophenyl)-3-[2-(2,3,4-trimethoxyphenoxy)ethenyl]-1,2,4-oxadiazole (cf. WO 93/01719).

Depending on the nature of the substituents, the compounds of the formula (I) can exist as geometric and/or optical isomers, or variously composed mixtures of isomers. The invention relates to the pure isomers and to the mixtures of isomers.

Furthermore, it has been found that the new 3-aryl-alkenyl-1,2,4-oxadiazole derivatives of the formula (I) are obtained by a) reacting an amide oxime derivative of the formula (II) and stereoisomers thereof

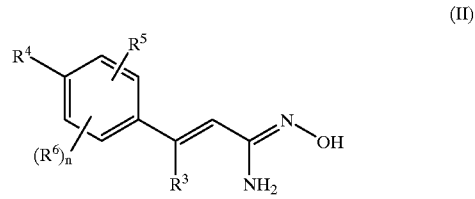

(II)

in which
$R^3$, $R^4$, $R^5$, $R^6$ and n have the abovementioned meanings
with carboxylic acid derivatives of the formulae (III), (IV) or (V)

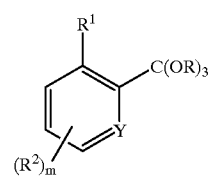

(III)

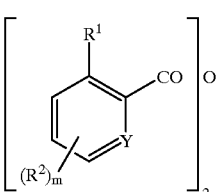

(IV)

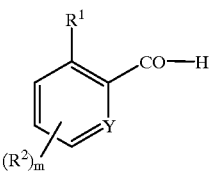

(V)

in which
  $R^1$, $R^2$, Y and m have the abovementioned meanings,
  R represents alkyl, in particular methyl or ethyl, and
  Hal represents halogen, such as fluorine, chlorine or bromine, preferably chlorine,
if appropriate in the presence of a diluent and if appropriate in the presence of a reaction auxiliary, or b) cyclizing compounds of the formula (VI)

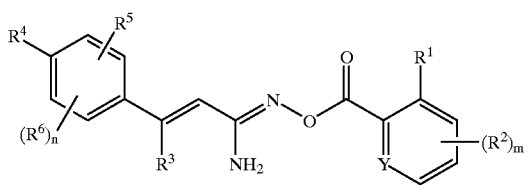

in which
Y, $R^1$, $R^2$, $R^3$, $R^4$, $R^5$, $R^6$, m and n have the abovementioned meanings,
in the presence of a diluent and if appropriate in the presence of a reaction auxiliary, or
c) reacting phosphonium halides of the formula (VII)

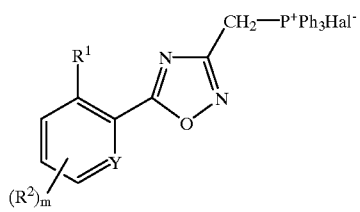

in which
$R^1$, $R^2$, Y and m have the abovementioned meanings and
Ph represents phenyl and
Hal represents chlorine, bromine or iodine, in particular chlorine and bromine, or
phosphonic esters of the formula (VIIa)

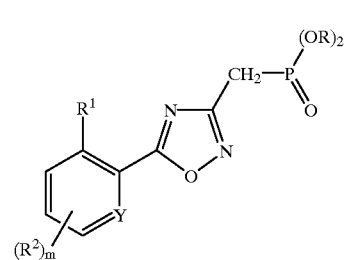

in which
$R^1$, $R^2$, Y and m have the abovementioned meanings and
R represents alkyl, in particular methyl or ethyl,
with aldehydes or ketones of the formula (VIII)

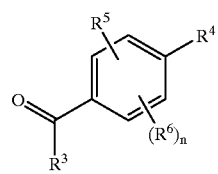

in which
$R^3$, $R^4$, $R^5$, $R^6$ and n have the abovementioned meanings, in the presence of a diluent and if appropriate in the presence of a reaction auxiliary.

Furthermore, it has been found that the new 3-aryl-alkenyl-1,2,4-oxadiazole derivatives of the formula (I) are highly suitable for combating animal pests. They are distinguished, in particular, by a powerful activity against arthropods and nematodes.

Surprisingly, the 3-aryl-alkenyl-1,2,4-oxadiazole derivatives of the formula (I) according to the invention display a considerably better activity against animal pests than the prior-art compounds having the most similar constitution.

Formula (I) provides a general definition of the compounds according to the invention.

Preferred substituents, or ranges of the radicals whose formulae are given hereinabove and hereinbelow will be illustrated in the following text.

$R^1$ preferably represents fluorine, chlorine, bromine, $C_1$–$C_6$-alkyl or $C_1$–$C_6$-alkoxy.

$R^2$ preferably represents hydrogen, fluorine, chlorine, bromine, $C_1$–$C_6$-halogenoalkyl or $C_1$–$C_6$-halogenoalkoxy.

$R^3$ preferably represents hydrogen or $C_1$–$C_4$-alkyl.

$R^4$ preferably represents fluorine, chlorine, bromine, tri-($C_1$–$C_8$-)-alkylsilyl-($C_1$–$C_6$-)-alkyl or tri-($C_1$–$C_8$)-alkylsilyl-($C_1$–$C_6$-)-alkoxy or a group —$A_k$—$R^7$, in which A represents oxygen, sulfur, SO, $SO_2$, $C_1$–$C_6$-alkylene, $C_1$–$C_6$-alkyleneoxy, $C_1$–$C_6$-alkylenethio, $C_1$–$C_6$-oxyalkylene, $C_1$–$C_6$-oxyalkyleneoxy, $C_1$–$C_6$-alkyleneoxy-$C_1$–$C_6$-alkylene, $C_2$–$C_5$-alkenediyl or $C_2$–$C_5$-alkinediyl, k represents a number 0 or 1 and $R^7$ represents $C_1$–$C_{20}$-alkyl, $C_2$–$C_{20}$-alkenyl or $C_2$–$C_{20}$-alkinyl, each of which is optionally monosubstituted or polysubstituted by fluorine and/or chlorine, or represents $C_3$–$C_{12}$-cycloalkyl which is optionally monosubstituted to trisubstituted by identical or different substituents, where, if appropriate, one or two $CH_2$ groups which are not directly adjacent to each other are replaced by oxygen and/or sulfur, or represents phenyl which is optionally monosubstituted to pentasubstituted by identical or different substituents, or pyridyl which is optionally monosubstituted to trisubstituted by identical or different substituents, suitable cycloalkyl, phenyl or pyridyl substituents being those mentioned below:

halogen,
$C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy which is optionally interrupted by a further 1–3 oxygen atoms,
$C_1$–$C_{18}$-alkylthio,
$C_1$–$C_8$-halogenoalkylthio,
3, 4-difluoromethylenedioxo,
3, 4-tetrafluoroethylenedioxo,
benzyliminooxymethyl which is optionally substituted by $C_1$–$C_4$-alkyl, $C_3$–$C_6$-cycloalkyl and/or halogen,
cyclohexyl and cyclohexyloxy, each of which is optionally substituted by $C_1$–$C_6$-alkyl, $C_1$–$C_6$-alkoxy, cyclohexyl and/or phenyl;
pyridyloxy which is optionally monosubstituted or disubstituted by identical or different substituents from the series consisting of halogen, $C_1$–$C_4$-alkyl or $C_1$–$C_4$-halogenoalkyl;

phenyl, benzyl, phenoxy, phenylthio, benzyloxy and benzylthio, each of which is optionally monosubstituted to disubstituted by identical or different substituents from the series consisting of $C_1$–$C_{12}$-alkyl, halogen, $C_1$–$C_4$-halogenoalkyl, $C_1$–$C_6$-alkoxy, $C_1$–$C_6$-halogenoalkoxy, $C_1$–$C_6$-alkoxy-$C_1$–$C_6$-alkyl, $C_1$–$C_6$-alkoxy-ethyleneoxy, $C_1$–$C_6$-alkylthio and/or $C_1$–$C_6$-halogenoalkylthio.

$R^5$ and $R^6$ independently of one another preferably represent hydrogen, fluorine, chlorine, bromine, $C_1$–$C_8$-alkyl, $C_1$–$C_8$-halogenoalkyl, $C_1$–$C_8$-alkoxy or $C_1$–$C_8$-halogenoalkoxy.

m preferably represents a number 1, 2 or 3.

n preferably represents a number 1 or 2.

Y preferably represents nitrogen or the group —$CR^9$, in which
$R^9$ represents hydrogen, fluorine, chlorine, bromine or $C_1$–$C_6$-alkyl.

$R^1$ particularly preferably represents fluorine, chlorine, bromine, $C_1$–$C_4$-alkyl or $C_1$–$C_4$-alkoxy.

$R^2$ particularly preferably represents hydrogen, fluorine, chlorine, bromine, $C_1$–$C_4$-halogenoalkyl or $C_1$–$C_4$-halogenoalkoxy.

$R^3$ particularly preferably represents hydrogen or methyl.

$R^4$ particularly preferably represents fluorine, chlorine, bromine, trimethylsilylmethyl, trimethylsilylmethoxy, dimethylethylsilylmethyl, dimethylethylsilylmethoxy, butyldimethylsilylmethyl, butyldimethylsilylmethoxy or a group —$A_k$—$R^7$ in which A represents oxygen, sulfur, SO, $SO_2$ or $C_1$–$C_4$-alkylene, $C_1$–$C_4$-alkyleneoxy, $C_1$–$C_4$-alkylenethio, $C_1$–$C_4$-oxyalkylene, $C_1$–$C_4$-oxyalkyleneoxy, $C_1$–$C_4$-alkyleneoxy-$C_1$–$C_4$-alkylene, in particular —$CH_2$—, —$CH_2CH_2$—, —$CH(CH_3)$—, —$CH_2CH_2CH_2$—, —$CH(CH_3)CH_2$—, —$C(CH_3)_2$—, —$CH_2CH_2CH_2CH_2$—, —$CH(CH_3)CH_2CH_2$—, —$CH_2CH(CH_3)CH_2$—, —$CH_2O$—, —$CH_2CH_2O$—, —$CH(CH_3)O$—, —$CH_2CH_2CH_2O$—, —$CH(CH_3)CH_2O$—, —$C(CH_3)_2O$—, —$CH_2CH_2CH_2CH_2O$—, —$CH(CH_3)CH_2CH_2O$—, —$CH_2CH(CH_3)CH_2O$—, —$OCH_2$—, —$CH_2S$—, —$OCH_2CH_2$—, —$OCH(CH_3)$—, $OCH_2CH_2CH_2$—, —$OCH(CH_3)CH_2$—, —$OC(CH_3)_2$—, —$OCH_2CH_2CH_2CH_2$—, —$OCH(CH_3)CH_2CH_2$— —$OCH_2CH(CH_3)CH_2$—; —$CH_2OCH_2$—, —$CH_2SCH_2$—, —$CH_2OCH_2CH_2$—, —$OCH_2O$—, —$OCH_2CH_2O$—, —$OCH(CH_3)O$—, —$OCH_2CH_2CH_2O$—, —$OCH(CH_3)CH_2O$—, —$OC(CH_3)_2O$—, —$OCH_2CH_2CH_2CH_2O$—, —$OCH(CH_3)CH_2CH_2O$— and —$CH_2CH(CH_3)CH_2O$— or $C_2$–$C_5$-alkenediyl or $C_2$–$C_5$-alkinediyl, k represents a number 0 or 1 and $R^7$ represents $C_1$–$C_{20}$-alkyl, $C_2$–$C_{20}$-alkenyl or $C_2$–$C_{20}$-alkinyl, each of which is optionally monosubstituted or polysubstituted by fluorine and/or chlorine, radicals which may be mentioned in particular being: methyl, ethyl, n-propyl, isopropyl, n-butyl, isobutyl, sec-butyl, tert-butyl, n-pentyl, isoamyl, neopentyl, n-hexyl, isohexyl, 3,3-dimethylbutyl, n-heptyl, 5-methylhexyl, 4-methylhexyl, 3-methylhexyl, 4,4-dimethylpentyl, n-octyl, 6-methylheptyl, n-nonyl, 7-methyloctyl, n-decyl, 8-methylnonyl, n-undecyl, 9-methyldecyl, n-dodecyl, 10-methylundecyl, n-tridecyl, 11-methyldodecyl, n-tetradecyl, 12-methyltridecyl, n-pentadecyl, 13-methyl-tetradecyl, n-hexadecyl, n-heptadecyl, n-octadecyl, n-nonadecyl, n-eicosyl, vinyl, propenyl, isopropenyl, butenyl, pentenyl, hexenyl, heptenyl, octenyl, 3-methyl-1-butenyl, ethynyl, propynyl, butynyl, pentynyl, hexynyl, 3,3-dimethyl-1-butynyl, 4-methyl-1-pentynyl, 3-methyl-1-pentynyl, 5-methyl-1-hexynyl, 4-methyl-1-hexynyl, 3-methyl-1-hexynyl, octynyl, nonynyl, decynyl, undecynyl, dodecynyl, tridecynyl, tetradecynyl, pentadecynyl and hexadecynyl, each of which is optionally monosubstituted or polysubstituted by fluorine and/or chlorine; $C_3$–$C_{10}$-cycloalkyl which is optionally monosubstituted to trisubstituted by identical or different substituents, in particular cyclopropyl, cyclobutyl, cyclopentyl, cyclohexyl, cycloheptyl and cyclooctyl, where optionally one or two $CH_2$ groups which are not directly adjacent to each other are replaced by oxygen and/or sulfur, phenyl which is optionally monosubstituted to pentasubstituted by identical or different substituents, or pyridyl which is optionally monosubstituted to trisubstituted by identical or different substituents, suitable cycloalkyl, phenyl and pyridyl substituents being those mentioned below:

F, Cl, Br, $C_1$–$C_{18}$-alkyl, $C_1$–$C_6$-alkoxy-$C_1$–$C_8$-alkyl, $C_1$–$C_8$-alkoxy which is monosubstituted to hexasubstituted by identical or different substituents from the series consisting of F and Cl, $C_1$–$C_2$-alkyl which is monosubstituted to pentasubstituted by identical or different substituents from the series consisting of F and Cl, $C_1$–$C_{18}$-alkoxy and —$(OC_2H_4)_{1-3}$—O—$C_1$–$C_6$-alkyl, $C_1$–$C_{12}$-alkylthio, $C_1$–$C_8$-alkylthio which is monosubstituted to hexasubstituted by identical or different substituents from the series consisting of F and Cl, 3,4-difluoromethylenedioxo, 3,4-tetrafluoroethylenedioxo, the groups

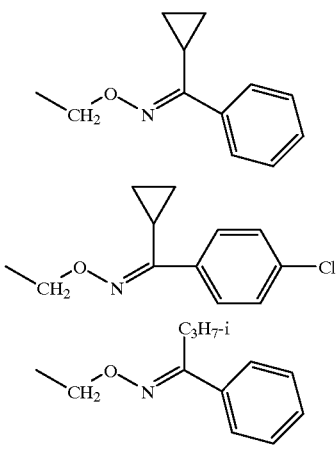

-continued

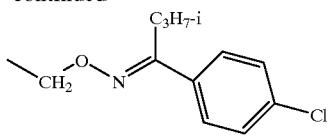

cyclohexyl and cyclohexyloxy, each of which is optionally substituted by $C_4$–$C_4$-alkyl, $C_1$–$C_4$-alkoxy, cyclohexyl and/or phenyl;

pyridyloxy which is optionally monosubstituted or disubstituted by identical or different substituents from the series consisting of F, Cl, and $CF_3$;

phenyl, benzyl, phenoxy, phenylthio, benzyloxy and benzylthio, each of which is optionally monosubstituted or disubstituted by identical or different substituents from the series consisting of $C_1$–$C_{12}$-alkyl, F, Cl, Br, $CF_3$, $C_1$–$C_4$-alkoxy, $C_1$–$C_4$-alkoxy which is monosubstituted to hexasubstituted by identical or different substituents from the series consisting of F and Cl, $C_1$–$C_4$-alkoxy-$C_1$–$C_4$-alkyl, $C_1$–$C_4$-alkoxy-ethyleneoxy, $C_1$–$C_4$-alkylthio and $C_1$–$C_4$-alkylthio which is monosubstituted to hexasubstituted by identical or different substituents from the series consisting of F and Cl.

$R^5$ and $R^6$ independently of one another particularly preferably represent hydrogen, fluorine, chlorine, bromine, $C_1$–$C_6$-alkyl, $C_1$–$C_6$-halogenoalkyl, $C_1$–$C_6$-alkoxy or $C_1$–$C_6$-halogenoalkoxy.

m particularly preferably represents a number 1, 2 or 3.

n particularly preferably represents a number 1 or 2.

Y particularly preferably represents a nitrogen atom or the group —$CR^9$ in which
  $R^9$ represents hydrogen, fluorine, chlorine, bromine or $C_1$–$C_6$-alkyl.

Alkyl radicals, hereinabove and in the following text, unless otherwise specified, and in connection with hetero atoms, such as, for example, in alkoxy and alkylthio, can be straight-chain or branched, as long as this is possible.

If m>1, the radicals $R^2$ can be identical or different. If n=2, the radicals $R^6$ can be identical or different.

Very particularly preferred compounds are those of the formula (I-a)

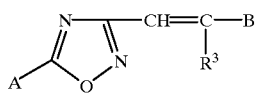

(I-a)

in which

A represents one of the radicals mentioned below

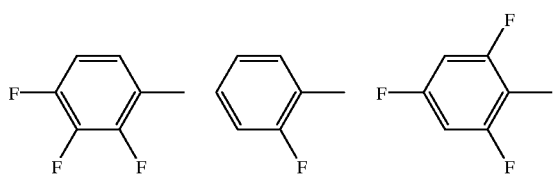

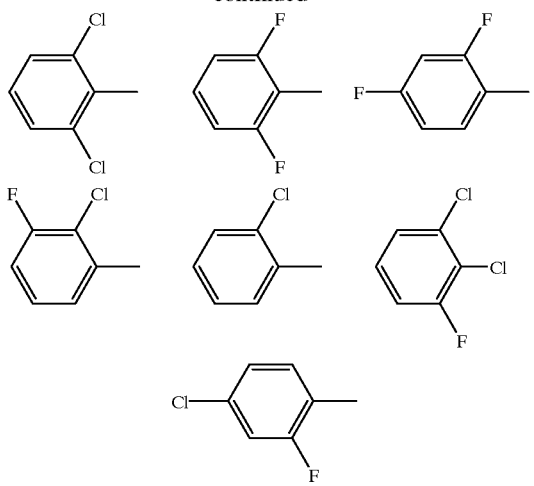

B represents one of the radicals

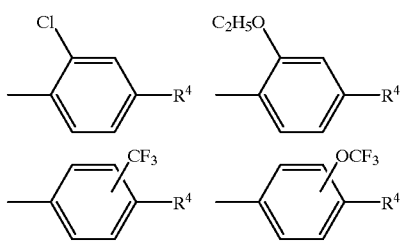

$R^3$ represents hydrogen or methyl and
$R^4$ has the abovementioned meaning.

In each case, the compounds 5-(2,4-dichlorophenyl)-3-[2-(2,4-dichlorophenyl)-ethenyl]-1,2,4-oxadiazole (cf. J. Heterocycl. Chem. 15 (8), 1373–8, 1978) and 5-(2,6-difluorophenyl)-3-[2-(2,3,4-trimethoxy-phenyl)ethenyl]-1,2,4-oxadiazole are excepted.

The definitions of radicals can be combined as desired, that is to say that combinations between the preferred and particularly preferred ranges are also possible. Preferred compounds of the formula (I) are those in which $R_1$, $R^2$, $R^3$, $R^4$, $R^5$, $R^6$, Y, m and n have the meanings mentioned as being preferred.

Particularly preferred compounds of the formula (I) are those in which $R^1$, $R^2$, $R^3$, $R^4$, $R^5$, $R^6$, Y, m and n have the meanings mentioned as being particularly preferred.

Examples of compounds of the formula (I) according to the invention are listed in Tables 1–7

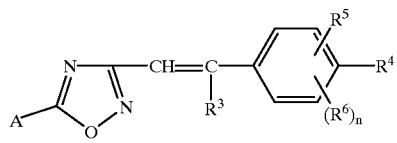

TABLE 1

| A | $R^3$ | ![aryl with $R^5$, $R^4$, $(R^6)_n$] |
|---|---|---|
| 2,6-diF-phenyl | H | 4-$C_4H_9$-t phenyl |
| 2,6-diF-phenyl | H | 4-$C_6H_{13}$-n phenyl |
| 2,6-diF-phenyl | H | 4-$C_{12}H_{25}$-n phenyl |
| 2,6-diF-phenyl | H | 4-$OCF_2$-$OCF_2$ phenyl |
| 2,6-diF-phenyl | H | 4-$OCH_2$-$CF_3$ phenyl |

TABLE 1-continued

| A | $R^3$ | ![aryl with $R^5$, $R^4$, $(R^6)_n$] |
|---|---|---|
| 2,6-diF-phenyl | H | 4-$OCF_2$-$CHFCH_3$ phenyl |
| 2,6-diF-phenyl | H | 4-$CH_2CH_2$-$OC_2H_5$ phenyl |
| 2,6-diF-phenyl | H | 4-$CH_2CH_2$-$OC_4H_9$ phenyl |
| 2,6-diF-phenyl | H | 4-$C_4H_9$-t, 3-$OC_2H_5$ phenyl |
| 2,6-diF-phenyl | H | 4-$C_4H_9$-t, 3-$OC_2H_5$ phenyl |
| 2,6-diF-phenyl | H | 4-cyclohexyl phenyl |
| 2,6-diF-phenyl | H | 4-phenoxy phenyl |

TABLE 1-continued

| A | R³ | (aryl group with R⁵, R⁴, (R⁶)ₙ) |
|---|---|---|
| 2,6-difluorophenyl | H | 4-(4-chlorophenoxy)phenyl |
| 2,6-difluorophenyl | H | 2,6-dichloro-4-(4-chlorophenoxy)phenyl |
| 2,6-difluorophenyl | H | 3,5-dichloro-2,4-difluorophenyl |
| 2,6-difluorophenyl | H | 3,5-dichloro-2,4-difluorophenyl (isomer) |
| 2,6-difluorophenyl | H | 2,3,5-trifluoro-4-(trifluoromethyl)phenyl |
| 2,6-difluorophenyl | H | 2,3,5-trifluoro-4-(trifluoromethoxy)phenyl |
| 2,6-difluorophenyl | H | 4-(n-butylthio)phenyl |
| 2,6-difluorophenyl | H | 4-(n-hexylthio)phenyl |
| 2,6-difluorophenyl | H | 4'-(trifluoromethoxy)biphenyl-4-yl |
| 2,6-difluorophenyl | H | 4'-(difluoromethoxy)biphenyl-4-yl |
| 2,6-difluorophenyl | H | 4'-chlorobiphenyl-4-yl |
| 2,6-difluorophenyl | H | 2'-chloro-3-fluoro-4'-(trifluoromethyl)biphenyl-4-yl |
| 2,6-difluorophenyl | H | 2,6-dichloro-4-[(3-chloro-5-(trifluoromethyl)pyridin-2-yl)oxy]phenyl |
| 2,6-difluorophenyl | H | 3,5-dichloro-4-(1,1,2,2-tetrafluoroethyl)phenyl |

TABLE 2
Compounds of the Table 1 in which
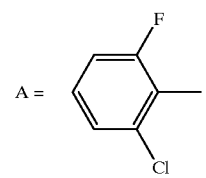
TABLE 3
Compounds of the Table 1 in which
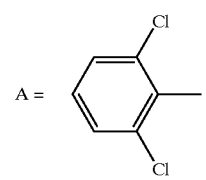

TABLE 4

Compounds of the Table 1 in which

A = 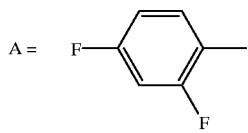

TABLE 5

Compounds of the Table 1 in which

A = 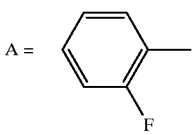

TABLE 6

Compounds of the Table 1 in which

A = 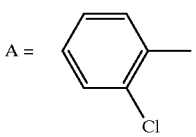

TABLE 7

Compound of the Tables 1–6 in which $R^3=Ch_3$.

If, for example, (E)-4-chloro-2-methylcinnamamide oxime and 1,3-difluoro-2-(triethoxymethyl)-benzene are used for carrying out the process a) according to the invention, the course of the reaction can be represented by the following equation:

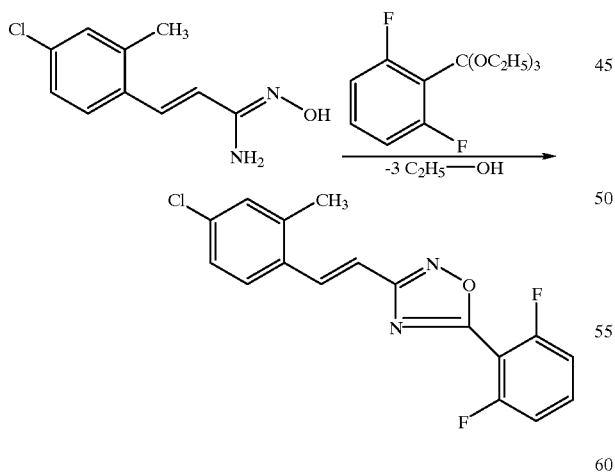

Formula (II) provides a general definition of the amide oximes required as starting substances for carrying out the process a) according to the invention. In this formula, $R^3$, $R^4$, $R^5$, $R^6$ and n preferably represent those radicals which have already been mentioned in connection with the description of the substances of the formula (I) according to the invention as being preferred for these substituents.

Some of the compounds of the formula (II) which are used as starting materials are known (cf. for example Cervena' et. al. Collect. Czech, Chem. Commun. 46 (1981) 5, pp. 1188–1198, EP 8 356, EP 7 529) or can be obtained by the processes described in these publications.

The compounds of the formula (II) are obtained, for example, when cinnamonitriles of the formula (X)

(X)

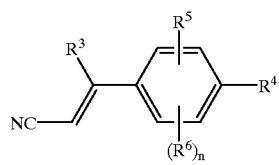

in which $R^3$, $R^4$, $R^5$, $R^6$ and n have the abovementioned meanings, are reacted with hydroxylamine or hydroxylamine hydrochloride, if appropriate in the presence of a diluent such as alcohols or water, or mixtures of these, and if appropriate in the presence of a base, such as alkali metal carbonates or alkali metal hydroxides, for example sodium carbonate, at a temperature between 20° C. and 150° C., preferably between 40° C. and 120° C.

The cinnamonitriles of the formula (X) are new and also part of the invention.

They can be prepared in a simple manner by known processes. For example, the cinnamonitriles of the formula (X) are obtained by A) reacting 3-aryl-2-chloropropionitriles of the formula (XI, (XI)

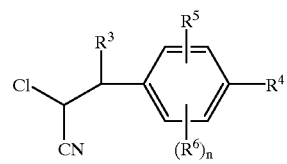

in which $R^3$, $R^4$, $R^5$, $R^6$ have the abovementioned meanings with a base, for example amines such as diazabicycloundecene, if appropriate in the presence of a diluent, for example ethers such as tetrahydrofuran, or B) by reacting aldehydes or ketones of the formula (VIII)

(VIII)

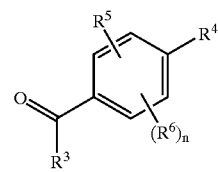

in which $R^3$, $R^4$, $R^5$, $R^6$ and n have the abovementioned meanings, with dialkyl cyanomethylphosphonates (for example diethyl cyanomethylphosphonate) in the presence of a base such as, for example, potassium hydroxide and in the presence of a diluent such as, for example, tetrahydrofuran.

The 3-aryl-2-chloropropionitriles of the formula (XI) are new and also part of the invention.

They can be prepared in a simple manner by known processes.

The 3-aryl-2-chloropropionitriles of the formula (XI) are obtained, for example, by diasotizing substituted anilines of the formula (XII)

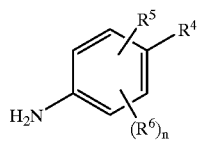
(XII)

in which
R⁴, R⁵, R⁶ and n have the abovementioned meanings, and treating the product with a catalyst, for example a mixture of copper(I) salts and copper(II) salts, in the presence of acrylonitrile.

Some of the compounds of the formulae (X) and (XI) themselves have arthropodicidal or nematicidal properties.

Formula (III) provides a general definition of the carboxylic orthoesters furthermore to be used as starting substances for carrying out the process a) according to the invention. The formulae (IV) and (V) provide general definitions of the carboxylic acid derivatives also suitable for carrying out the process a) according to the invention. In formulae (III) to (V), $R^1$, $R^2$, Y and m have the meanings which have already been mentioned in connection with the description of the substances of the formula (I) according to the invention as being preferred for these substituents. The carboxylic ortho esters of the formula (III) and the carboxylic acid derivatives of the formulae (IV) and (V) are generally known compounds of organic chemistry.

The compounds of the formulae (II) and (III) are preferably reacted in the presence of an acidic catalyst. Suitable acidic catalysts are virtually all mineral acids or Lewis acids. The mineral acids preferably include hydrohalic acids such as hydrofluoric acid, hydrochloric acid, hydrobromic acid or hydroiodic acid, and also sulfuric acid, phosphoric acid, phosphorous acid and nitric acid, and the Lewis acids preferably include aluminum(III) chloride, boron trifluoride or its etherate, titanium(IV) chloride and tin(IV) chloride.

The following Lewis acids are particularly preferably employed: boron trifluoride or its etherate, and aluminum (III) chloride.

When employing compounds of the formula (III), process a) is generally carried out in such a manner that compounds of the formula (II) are combined with an excess of compound of the formula (III), and the mixture is heated in the presence of an acidic catalyst. The compound of the formula (11) can simultaneously act as a diluent. The reaction time is approximately 1 to 4 hours. The reaction is generally carried out at temperatures between +20° C. and +200° C., preferably between +100° C. and +155° C. The process is preferably carried out at the pressure which is established under the reaction conditions when the mixture is heated at the reaction temperature required.

Preferably, the compounds of the formula (II) are reacted with the compounds of the formulae (IV) and (V), respectively, in the presence of a base.

Suitable bases are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides such as magnesium oxide and calcium oxide, moreover alkali metal carbonates and alkaline earth metal carbonates, such as sodium carbonate, potassium carbonate and calcium carbonate, and also alkali metal hydroxides and alkaline earth metal hydroxides such as sodium hydroxide and potassium hydroxide.

The reaction of the compounds of the formula (II) with the compounds of the formulae (IV) and (V), respectively, is generally carried out in the presence of a diluent.

Diluents which can be employed are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylic esters, such as ethyl acetate, and also strongly polar solvents such as dimethyl sulfoxide and sulfolane. The reaction can also be carried out in the presence of water if the acid halide is sufficiently stable to hydrolysis.

When employing the compounds of the formula (IV) or (V), process a) is generally carried out in such a manner that compounds of the formula (II) are stirred with an equimolar amount or an excess of the compound of the formula (IV) or (V) in the presence of a diluent and in the presence of an at least equimolar amount of base at temperatures between –20° C. and 150° C., preferably between 0° C. and 100° C., until the reaction has ended.

When the reaction is complete, the reaction mixture is cooled and concentrated in vacuo, and the residue which remains is taken up in an organic solvent and worked up in a manner known per se. The products obtained can be purified in the customary manner by recrystallization, distillation in vacuo or column chromatography (cf. also the preparation examples).

If, for example, (E)-4-cyclohexylcinnamamide oxime and, as carboxylic acid derivative of the formula (V), 2,6-difluorobenzoyl chloride are used as alternatives when carrying out process a) according to the invention, the course of the reaction can also be represented by the following equation:

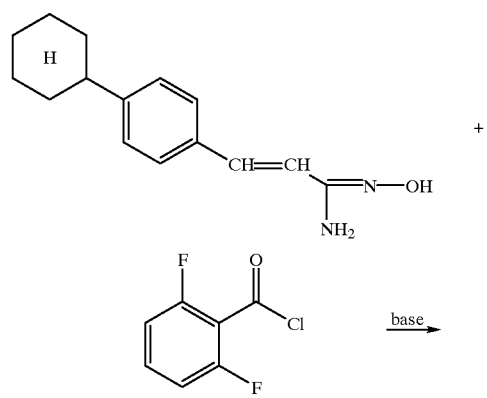

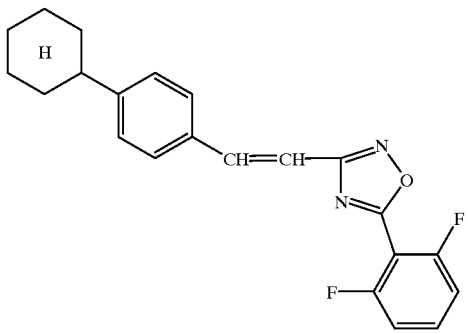

If, in process b), (E)-cyclohexylcinnamamide O-(2,6-difluorobenzoyl)-oxime is employed as compound of the formula (VI), the process can be described by the following equation:

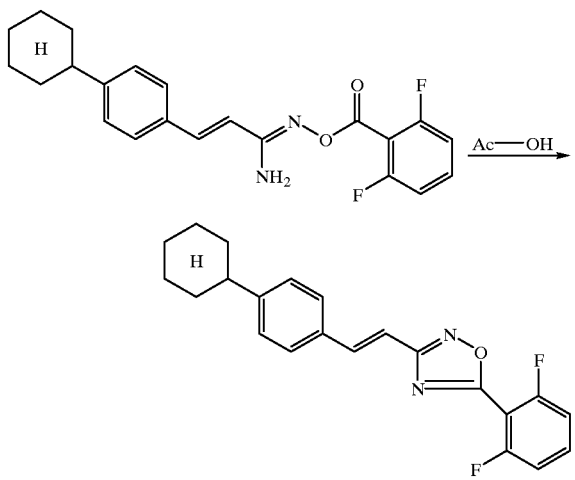

Compounds of the formula (IV) which are preferably employed in process b) are those in which the radicals $R^1$, $R^2$, $R^3$, $R^4$, $R^5$, $R^6$, n, m and Y have the meanings mentioned in the case of the compounds of the formula (I) as being preferred and particularly preferred.

The compounds of the formula (VI) can, in process a), be formed in situ from compounds of the formula (II) and suitable carboxylic acid derivatives of the formulae (III), (IV) and (V), but they can also be employed in the isolated form as shown here in process b).

Cyclization of the compounds of the formula (IV) is preferably carried out using diluents and, if appropriate, in the presence of a reaction auxiliary.

Suitable diluents for carrying out process b) according to the invention are all inert organic solvents.

Examples which may be mentioned are: halogenohydrocarbons, in particular chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, diflurobenzene, 1,2-dichloroethane, chlorobenzene, dichlorobenzene, chlorotoluene and trichlorobenzene; alcohols such as methanol, ethanol, isopropanol and butanol; ethers such as ethyl propyl ether, methyl tert-butyl ether, n-butyl ether, di-n-butyl ether, diisobutyl ether, di-iso-amyl ether, di-isopropyl ether, anisole, phenetol, cyclohexyl methyl ether, diethyl ether, ethylene glycol dimethyl ether, tetrahydrofuran, dioxane and dichlorodiethyl ether, nitrohydrocarbons such as nitromethane, nitroethane, nitrobenzene, chloronitrobenzene and o-nitrotoluene; nitriles such as acetonitrile, butyronitrile, isobutyronitrile, benzonitrile and m-chlorobenzonitrile; aliphatic, cycloaliphatic or aromatic hydrocarbons such as heptane, hexane, nonane, cymene, benzine fractions within a boiling range of 70° C. to 190° C., cyclohexane, methylcyclohexane, petroleum ether, ligroin, octane, benzene, toluene and xylene; esters such as ethyl acetate and isobutyl acetate; amides, for example formamide, N-methyl ethyl ketone, carboxylic acids such as acetic acid, propionic acid and butyric acid. Mixtures of the abovementioned solvents and diluents are also suitable.

Preferred substances are carboxylic acids such as acetic acid, or aromatic hydrocarbons such as toluene and xylene.

Reaction auxiliaries which can be used are also suitable dehydrating reagents such as, for example, dicyclohexylcarbodiimide [DCC] (cf., for example, F. Eloy Fortschr. chem. Forsch. 4 (1965) p. 807).

Process b) is generally carried out in such a manner that compounds of the formula (VI) are heated in a suitable diluent, if appropriate in the presence of a suitable reaction auxiliary. The reaction time is approximately 1 to 10 hours. In general, the reaction is carried out at temperatures between +20° C. and +200° C., preferably between +70° C. and +170° C. The process is preferably carried out at the pressure which is established under the reaction conditions when the mixture is heated at the reaction temperature required.

When the reaction is complete, the reaction mixture is cooled, and the entire reaction batch is concentrated, taken up in an organic solvent and worked up in a manner known per se. The products obtained can be purified in the customary manner by recrystallization, distillation in vacuo or column chromatography (cf. also the preparation examples).

If, in process c) for the preparation of the new 1,2,4-oxadiazole derivatives of the formula (I), 3-(diethoxyphosphonomethyl)-5-(2,6-difluorophenyl)-1,2,4-oxadiazole is employed as compound of the formula (VIIa) and 4-(4-trifluoromethoxyphenyl)-benzaldehyde as compound of the formula (VIII), the process can be represented by the following equation:

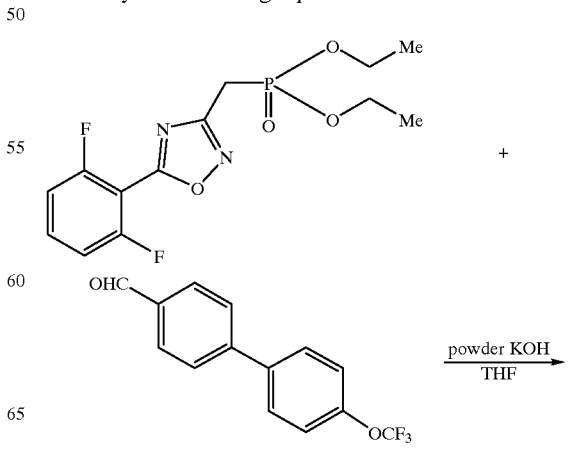

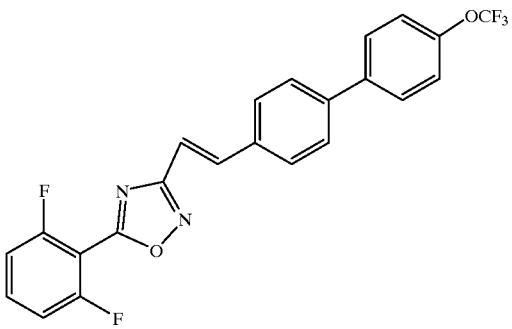

Formulae (VII) and (VIIa) provide general definitions of the 3,5-disubstituted 1,2,4-oxadiazoles required as starting substances for carrying out process c) according to the invention. In these formulae, Y, $R^1$, $R^2$ and m preferably represent those radicals which have already been mentioned in connection with the description of the substances of the formula (I) according to the invention as being preferred for these substituents.

The compounds of the formula (VII) used as starting materials are new and also part of the invention.

The new phosphonium halides of the formula (VII) are obtained when 3-halogenomethyl-1,2,4-oxadiazoles of the formula (IX)

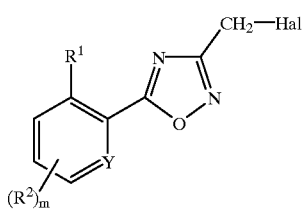

(IX)

in which
$R^1$, $R^2$, Y and m have the abovementioned meanings and
Hal represents fluorine, chlorine or bromine, in particular chlorine or bromine, are reacted with triphenylphosphine, if appropriate in the presence of a diluent.

Suitable diluents are all inert organic solvents. Examples which may be mentioned are: ethers, such as ethyl propyl ether, methyl tert-butyl ether, n-butyl ether, di-n-butyl ether, di-isobutyl ether, di-iso-amyl ether, di-isopropyl ether, anisole, phenetol, cyclohexyl methyl ether, diethyl ether, ethylene glycol dimethyl ether, tetrahydrofuran, dioxane; nitriles, such as acetonitrile, butyronitrile, isobutyronitrile, benzonitrile, aliphatic, cycloaliphatic or aromatic hydrocarbons, such as heptane, hexane, nonane, cymene, benzine fractions within a boiling range from 70° C. to 190° C., cyclohexane, methylcyclohexane, petroleum ether, ligroin, octane, benzene, toluene and xylene.

Ethers, such as dioxane and tetrahydrofuran; nitriles, such as acetonitrile, as well as toluene and benzene are preferred.

In general, the reaction is carried out in such a manner that compounds of the formula (IX) are combined with triphenylphosphine in a suitable diluent and the mixture is heated. The reaction time is 1 to 24 hours. When the reaction has ended, the reaction mixture is worked up in the customary manner.

Some of the compounds of the formula (IX) to be used as starting materials for the preparation of the new phosphonium halides of the formula (VII) are known (cf., for example, German Offenlegungschrift 24 06 786, GB 2 205 101. G. Palazzo, J. Heterocyclic Chem 16 (1979) p. 1469) or can be obtained by the processes described in these publications.

The new compounds of the formula (IX) are the subject-matter of an earlier, but unpublished, patent application and can be prepared as described therein.

Some of the phosphonic esters of the formula (VIIa) furthermore to be used as starting materials in process c) according to the invention as an alternative are known (cf., for example, European Offenlegungschrift 123 378, J. Chem. Soc., Perkin Trans. 1, (11), 2047–57, 1989) and/or can be obtained by the processes described therein, for example by heating the 3-halogenomethyl-1,2,4-oxadiazoles of the formula (IX) with triethyl phosphite, if appropriate in the presence of a diluent (cf. also the preparation examples).

Process c) according to the invention is preferably carried out using diluents and in the presence of bases.

Suitable diluents for carrying out process c) according to the invention are inert organic solvents as they are generally customary under the conditions of a Wittig reaction (cf. Houben Weyl, Methoden der Organischen Chemie, [Methods in Organic Chemistry] Volume X/4, p. 68). Examples which may be mentioned are alcohols, such as, for example, methanol, ethanol, isopropanol or butanol; amides such as, for example, dimethylformamide, dimethylacetamide and N-methyl-pyrrolidone, and also dimethyl sulfoxide, tetramethylene sulfone and hexamethylphosphoric triamide.

Process c) according to the invention is preferably carried out using bases. Examples of bases which can be employed are: hydroxides and alcoholates of lithium, sodium, potassium, magnesium, calcium and barium; furthermore other basic compounds such as trimethylamine, tribenzylamine, triisopropylamine, tributylamine, tribenzylamine, tricyclohexylamine, triamylamine, trihexylamine, N,N-dimethyl-aniline, N,N-dimethyl-toluidine, N,N-dimethyl-p-aminopyridine, N-methyl-pyrrolidone, N-methylpiperidine, N-methyl-imidazole, N-methylpyrrol, N-methyl-morpholine, N-methyl-hexamethyleneimine, pyridine, quinoline, β-picoline, isoquinoline, pyrimidine, acridine, N,N,N',N'-tetramethylenediamine, N,N,N',N'-tetraethylenediamine, quinoxaline, N-propyl-diisopropylamine, N,N'-dimethyl-cyclohexylamine, 2,6-lutidin, 2,4-lutidin, triethylendiamine, diazabicyclooctane (DABCO), diazabicyclononene (DBN) or diazabicycloundecene (DBU) and amides such as sodium amide and potassium amide.

In general, process c) according to the invention is carried out in such a manner that compounds of the formula (VII) or (VIIa) are combined with a small excess of compounds of the formula (VIII) and the mixture is heated in the presence of a base. The reaction time is approximately 5 to 30 hours. The reaction is generally carried out at temperatures between +20° C. and +200° C., preferably between +70° C. and +170° C. It is preferably carried out at the pressure which is established under the reaction conditions when the mixture is heated at the reaction temperature required.

When the reaction is complete, the reaction mixture is cooled and worked up in a manner known per se. The products obtained can be purified in the customary manner by recrystallization, distillation in vacuo or, preferably, by column chromatography. (cf. also the preparation examples).

Formula (VIII) provides a general definition of the aldehydes and ketones furthermore required as starting substances for carrying out process c) according to the invention. In this formula, $R^3$, $R^4$, $R^5$, $R^6$ and n preferably represent those radicals which have already been mentioned in connection with the description of the substances of the formula (I) according to the invention as being preferred for these substituents.

The compounds of the formula (VIII) are generally known compounds of organic chemistry.

In those compounds of the formula (I), synthesized by processes a) to c), in which $R^4$ represents a group which has sulfur attached to it, this group can be oxidized. The oxidation can be carried out by customary processes using suitable oxidants, such as peroxides (for example $H_2O_2$), permanganate, perbenzoic acid, or a mixture of potassium peroxymonosulfate, 2 $KHSO_5.KHSO_4$, and a solvent or solvent mixture (for example water, acetic acid, methanol) (cf. A. R. Katritzky, C. W. Rees in Comprehensive Heterocyclic Chemistsry, Pergamon Press, Oxford, N.Y., 1984, Vol. 3, p. 96; D. J. Brown et al. Chem. Soc. (C), 1971, p. 256).

The oxidation may also be initiated or accelerated by means of catalysts.

The active compounds are suitable for combating animal pests, preferably arthropods and nematodes, in particular insects and arachnids encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp,.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for exmple, *Acarus siro,* Argas spp., Ornithodoros spp., *Dermanyssus gallinae, Erio-*

*phyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., The plant—parasitic nematodes include Pratylenchus spp., *Radopholus similis, Ditylenchus dipsaci, Tyulenchulus semipenetrans,* Heterodera spp., Meloidogyne spp., Aphelenchoides spp., Longidorus spp., Xiphinema spp., Trichodorus spp.

The active compounds can be converted to the customary formulations, such as solutions, emulsions, wettable powders, suspensions, powders, dusts, pastes, soluble powders, granules, suspoemulsion concentrates, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The following compounds may be mentioned:

acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, Alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mevinphos, mesulfenphos, methacrifos, methamidophos, naled, omethoate, oxydemeton M, oxydeprofos, parathion A, parathion M, phenthoate, phorate, phosalone, phosmet, phosphamidon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridinyl) methyl]-N'-cyano-N-methyl-ethaneimideamide (NI-25), abamectin, amitrazin, avermectin, azadirachtin, bensultap, Bacillus thuringiensis, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimiphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivermectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-3-carbonitrile (AC 303630).

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds according to the invention are not only active against plant, hygiene and stored-product pests, but also, in the veterinary medicine sector, against animal parasites (ectoparasites and endoparasites) such as scaly ticks, Argasidae, scab mites, Trombidae, flies (stinging and sucking), parasitic fly larvae, lice, hair lice, bird lice, fleas and endoparasitic worms. For example, they show an outstanding activity against ticks such as, for example, boophilus microplus.

The active compounds of the formula (I) according to the invention are also suitable for combating arthropods which infest agricultural productive lifestock such as, for example, cattle, sheep, goats, horses, pigs, donkeys, camels, buffalo, rabbits, chickens, turkeys, ducks, geese, honeybees, other domestic animals such as, for example, dogs, cats, cage birds, aquarium fish, as well as so-called laboratory animals such as, for example, hamsters, guineapigs, rats and mice. By combating these arthropods, it is intended to reduce deaths and declining performance (in meat, milk, wool, hides, eggs, honey and the like), so that more economic and simpler animal husbandry is made possible by the use of the active compounds according to the invention.

The application of the active compounds according to the invention occurs in the veterinary sector in a known fashion by enteral application in the form of, for example, tablets, capsules, potions, drenches, granules, pastes, boli, the feed-through process, suppositories, by parenteral application, such as, for example, by means of injections (intramuscular, subcutaneous, intraveneous, intraperitoneal and the like), by implants, by nasal application, by dermal administration, for example in the form of bathing or dipping, spraying, pouring on and spotting on, by washing, dusting, and with the aid of molded articles containing active compound, such as collars, ear tags, tail tags, limb bands, halters, marking devices and the like.

Preparation and use of the substances according to the invention are illustrated by the examples which follow.

Preparation Examples
EXAMPLE I-1

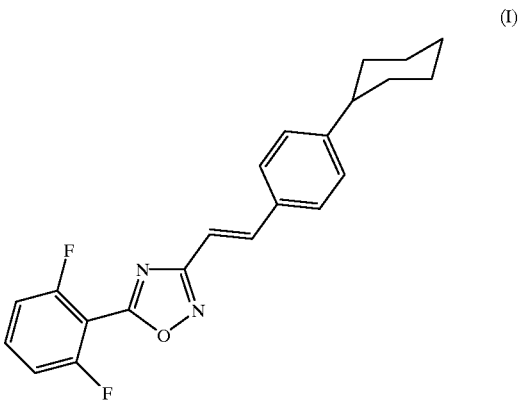

(I)

3.0 g (7.8 mmol) of (E)-cyclohexylcinnamamide O-(2,6-difluorobenzoyl)-oxime are heated in 10 ml of glacial acetic acid until cyclization is complete (approximately 1 hour). The entire reaction mixture is then concentrated in vacuo, the product is taken up in ethyl acetate and washed with water, and the organic phase is dried over sodium sulfate. The solvent is subsequently distilled off in vacuo, and the crude product which remains is recrystallized from isopropanol.

1.2 g (41.9% of theory) of (E)-3-(4-cyclohexyl-styryl)-5-(2,6-difluorophenyl)-1,2,4-oxadiazole of melting point 86–87° C. are obtained.

EXAMPLE I-2

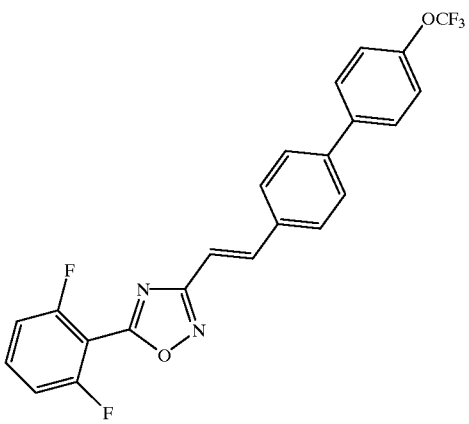

A solution of 1.2 g (3.6 mmol) of 3-(diethoxyphosphonomethyl)-5-(2,6-difluorophenyl)-1,2,4-oxadiazole in 10 ml of tetrahydrofuran is added dropwise to a suspension of 0.43 g (7.7 mmol) of pulverulent potassium hydroxide in 20 ml of tetrahydrofuran and 1.0 g (3.9 mol) of 4-(4-trifluoromethoxyphenyl)-benzaldehyde. Stirring is then continued for 20 minutes at room temperature, and the solid which precipitates during this process is filtered off and washed with tetrahydrofuran. The filtrate is concentrated in vacuo, and the residue which remains is recrystallized from isopropanol.

0.8 g (48.8% of theory) of (E)-3-[4-(4-trifluoromethoxyphenyl)-styryl]-5-(2,6-difluorophenyl)-1,2,4-oxadiazole of melting point 122 to 123° C. is obtained.

EI MS m/z (%) 444 (M$^+$, 100)

The compounds of the formula (I) listed in Table 8 below can be prepared analogously and in accordance with the general preparation instructions.

TABLE 8
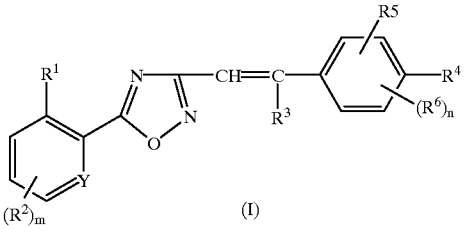
| Ex. No. | $R^1$, $(R^2)_m$, Y | $R^3$ | $R^5$, $R^4$, $(R^6)_n$ | Physical constants |
|---|---|---|---|---|
| I-3 | 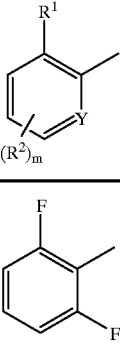 2,6-diF | H | 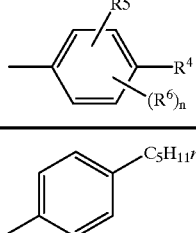 4-$C_5H_{11}n$ | 354 ($M^+$, 48) |
| I-4 | 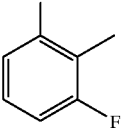 2,6-diF | H | 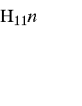 4-$C_7H_{15}n$ | m.p.: 54–55° C. |
| I-5 | 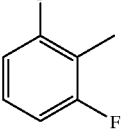 2-F, 6-Cl | H | 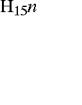 4-$C_7H_{15}n$ | m.p.: oil |
| I-6 | 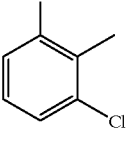 2,6-diF | H |  4-$C_{10}H_{21}n$ | m.p.: 59° C. |
| I-7 | 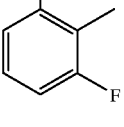 2,6-diF | H |  4-$C_{12}H_{25}n$ | m.p.: 01 |
| I-8 | 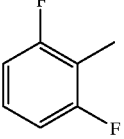 2,6-diF | H | 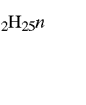 4-(4-$OCF_3$-phenoxy) | m.p.: 99–100° C. |
| I-9 | 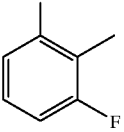 2-F, 6-Cl | H | 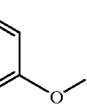 4-(4-$OCF_3$-phenoxy) | m.p.: 70–72° C. |

TABLE 8-continued
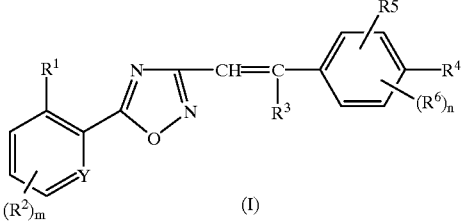
(I)
| Ex. No. | 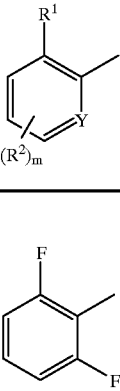 (R²)ₘ | R³ | 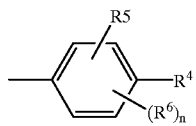 (R⁶)ₙ | Physical constants |
|---|---|---|---|---|
| I-10 | 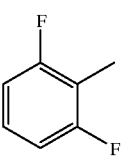 | H | 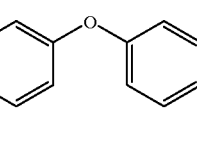 | m.p.: 92–94° C. |
| I-11 | 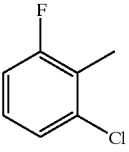 | H | 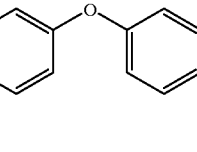 | m.p.: 108–109° C. |
| I-12 | 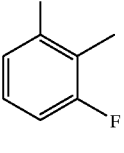 | H | 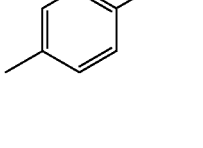 | m.p.: 74–76° C. |
| I-13 | 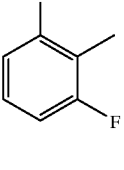 | H | 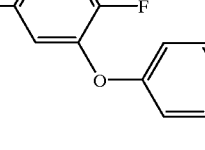 | m.p.: 146–148° C. |
| I-14 | 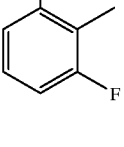 | H | 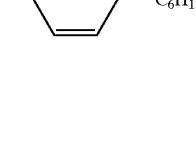 | m.p.: 52–54° C. |
| I-15 | 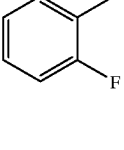 | H | 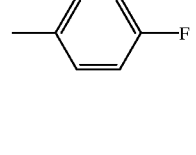 | m.p.: 178–179° C. |

TABLE 8-continued
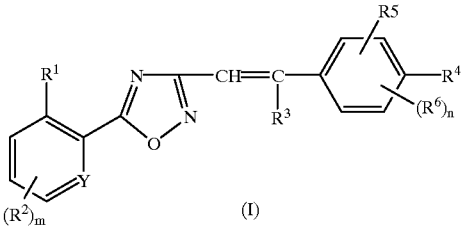
| Ex. No. | 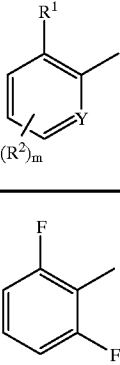 | R³ |  | Physical constants |
|---|---|---|---|---|
| I-16 | 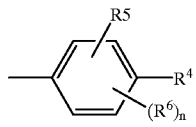 | H | 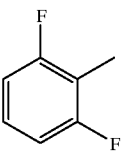 | m.p.: 131–132° C. |
| I-17 | 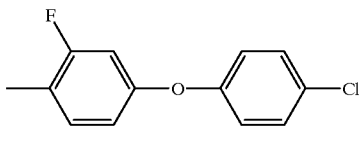 | H | 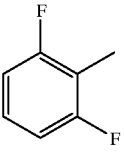 | m.p.: 80–81° C. |
| I-18 | 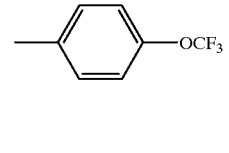 | H | 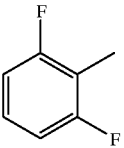 | m.p.: 121–123° C. |
| I-19 | 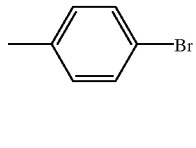 | H | 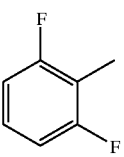 | m.p.: 165–166° C. |
| I-20 | 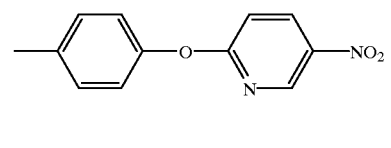 | H | 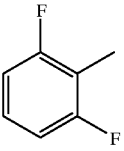 | m.p.: 125° C. |

TABLE 8-continued

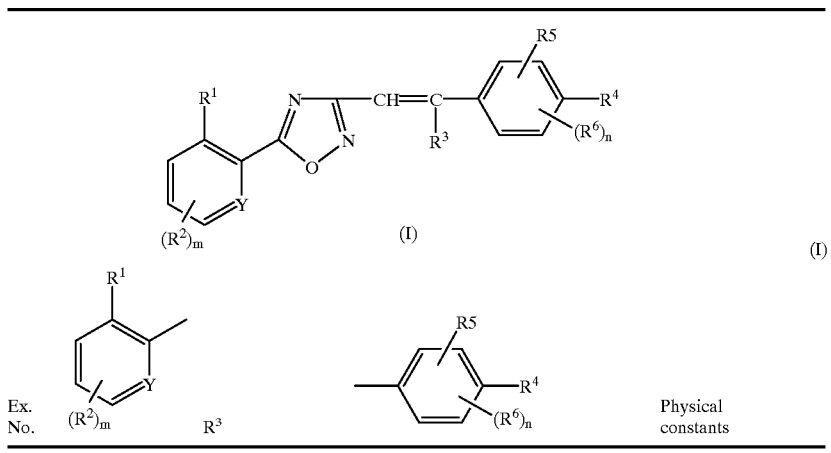

| Ex. No. | R¹ (R²)ₘ Y | R³ | R⁴ R⁵ (R⁶)ₙ | Physical constants |
|---|---|---|---|---|
| I-21 | 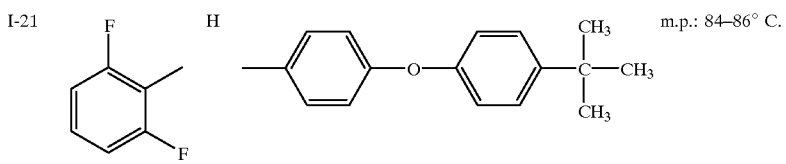 | H | | m.p.: 84–86° C. |
| I-22 | 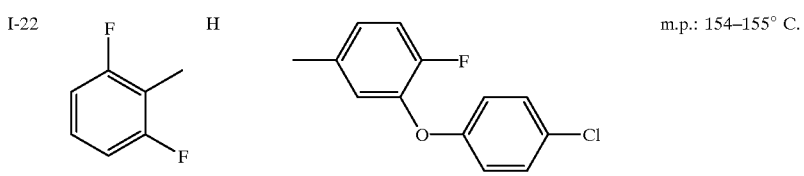 | H | | m.p.: 154–155° C. |
| I-23 | 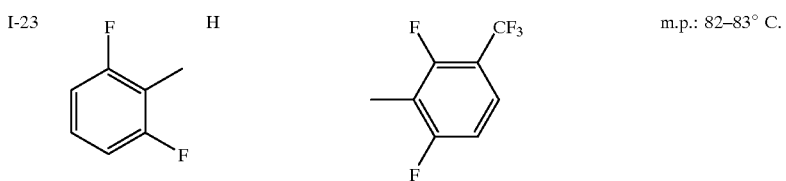 | H | | m.p.: 82–83° C. |

EI MS (M/Z in %)

Starting Substances of the Formula (II)

EXAMPLE (II-1)

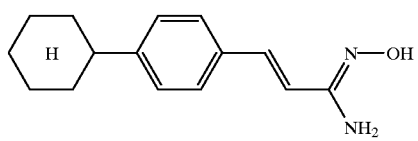

A solution of 13.9 g (0.2 mol) of hydroxylamine hydrochloride, 21.1 g (0.2 mol) of sodium carbonate and 20.0 g (0.095 mol) of (E)-4-cyclohexyl-cinnamonitrile is stirred in 50 ml of ethanol and 100 ml of water at reflux temperature until the reaction is complete (approximately 24 hours). The entire reaction batch is then introduced into water and extracted using methylene chloride.

19.6 g (84.4% of theory) of (E)-4-cyclohexyl-cinnamamide oxime are obtained.

$^1$H NMR (400 MHz, CDCl$_3$, δ): 4.75 (br. s, 2H, —NH$_2$); 6.44; 6.81 (2d, 2H, 2×—CH═; J$_{H,H}$=16.5 Hz) ppm The compounds of the formula (II) listed in Table 9 below can be prepared analogously.

TABLE 9

Compound of the formula (II)

$$\text{(II)}$$

| Ex. No. | $R^3$ | Ar ($R^5$, $R^4$, $(R^6)_n$) | Physical constants |
|---|---|---|---|
| II-2 | H | 4-n-C$_5$H$_{11}$-C$_6$H$_4$- | 4.74 (br. s, 2H, —NH$_2$)[a] |
| II-3 | H | 4-n-C$_6$H$_{13}$-C$_6$H$_4$- | 4.76 (br. s, 2H, —NH$_2$)[a] |
| II-4 | H | 4-n-C$_7$H$_{15}$-C$_6$H$_4$- | 4.79 (br. s, 2H, —NH$_2$)[a] |
| II-5 | H | 4-n-C$_{10}$H$_{21}$-C$_6$H$_4$- | 4.72 (br. s, 2H, —NH$_2$)[a] |
| II-6 | H | 4-n-C$_{12}$H$_{25}$-C$_6$H$_4$- | 4.8 (br. s, 2H, —NH$_2$)[a] |
| II-7 | H | 4-n-C$_{14}$H$_{29}$-C$_6$H$_4$- | 3.12 (br. s, 2H, —NH$_2$)[a] |

TABLE 9-continued

Compound of the formula (II)

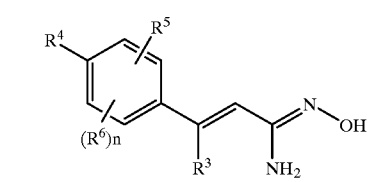

| Ex. No. | R³ | 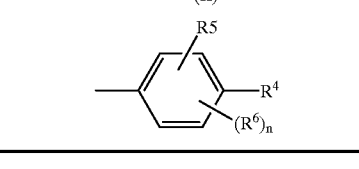 | Physical constants |
|---|---|---|---|
| II-8 | H | 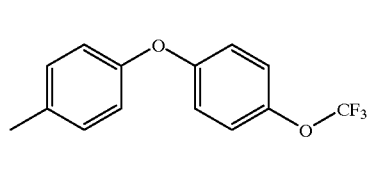 | 4.82 (br. s, 2H, —NH₂)ᵃ⁾ |
| II-9 | H | | 4.83 (br. s, 2H, —NH₂)ᵃ⁾ |
| II-10 | H | | 4.82 (br. s, 2H, —NH₂)ᵃ⁾ |
| II-11 | H | | 4.83 (br. s, 2H, —NH₂)ᵇ⁾ |

ᵃ⁾¹H NMR (400 MHz, CDCl₃, δ;
ᵇ⁾¹H NMR (400 MHz, DMSO-d₆, δ) in ppm

EXAMPLE (VI-1)

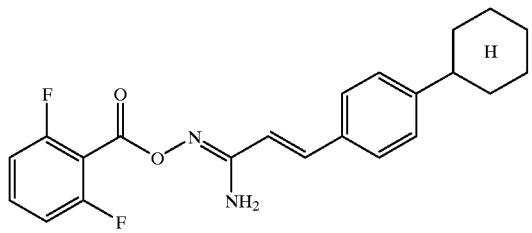

9.8 g (0.04 mol) of (E)-4-cyclohexyl-cinnamamide oxime and 9.8 ml of pyridine are introduced into 50 ml of chloroform, and 8.5 g (0.048 mol) of 2,6-difluorobenzoyl chloride in 20 ml of chloroform are added dropwise at 0° C. to 5° C. After the mixture has been stirred for approximately twelve hours at room temperature, it is filtered, and the entire reaction batch is concentrated in vacuo. Water is subsequently added, and the solid which precipitates during this process is filtered off with suction. After recrystallization from ispropanol, 3.6 g (23.4% of theory) of (E)-4-cyclohexylcinnamamide O-(2,6-difluorobenzoyl)-oxime of melting point 164–165° C. are obtained.

The compounds of the formula (VI) listed in Table 10 below can be prepared analogously.

TABLE 10
Compounds of the formula (VI)
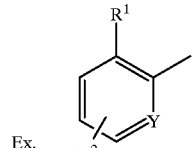
(VI)
| Ex. No. | (R²)ₘ, Y | R³ | R⁵, R⁴, (R⁶)ₙ | Physical constants |
|---|---|---|---|---|
| VI-2 | 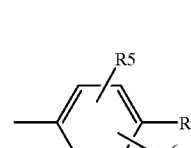 | H | 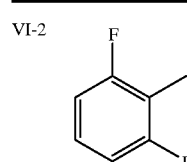 $C_5H_{11}n$ | 5.18 (br. s, 2H, —NH$_2$)[a] |
| VI-3 | 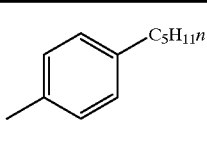 | H | 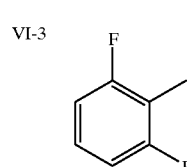 $C_7H_{15}n$ | 5.07 (br. s, 2H, —NH$_2$)[a] |
| VI-4 | 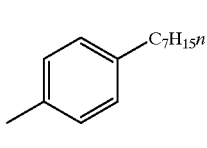 | H | 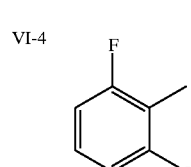 $C_7H_{15}n$ | 5.06 (br. s, 2H, —NH$_2$)[a] |
| VI-5 | 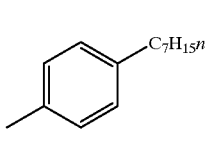 | H | 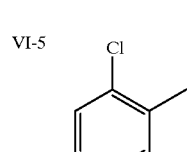 $C_7H_{15}n$ | 5.05 (br. s, 2H, —NH$_2$)[a] |
| VI-6 | 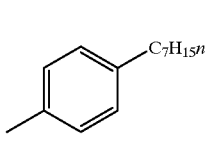 | H | 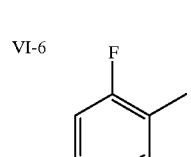 $C_{10}H_{21}n$ | 5.07 (br. s, 2H, —NH$_2$)[a] |
| VI-7 | 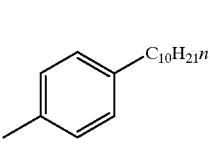 | H | 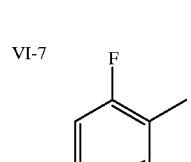 $C_{12}H_{25}n$ | 5.06 (br. s, 2H, —NH$_2$)[a] |

TABLE 10-continued
Compounds of the formula (VI)
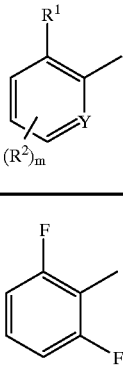
(VI)
| Ex. No. | $R^1$ $(R^2)_m$ $Y$ | $R^3$ | $R^5$ $R^4$ $(R^6)_n$ | Physical constants |
|---|---|---|---|---|
| VI-8 | 2,6-diF phenyl | H | 4-($n$-C$_{14}$H$_{29}$)phenyl | 5.05 (br. s, 2H, —NH$_2$)$^{a)}$ |
| VI-9 | 2,6-diF phenyl | H | 4-(4-CF$_3$-phenoxy)phenyl | 5.17 (br. s, 2H, —NH$_2$)$^{a)}$ |
| VI-10 | 2-F, 6-Cl phenyl | H | 4-(4-CF$_3$-phenoxy)phenyl | 5.43 (br. s, 2H, —NH$_2$)$^{a)}$ |
| VI-11 | 2,6-diF phenyl | H | 4-(4-OCF$_3$-phenoxy)phenyl | 5.12 (br. s, 2H, —NH$_2$)$^{a)}$ |

TABLE 10-continued

Compounds of the formula (VI)

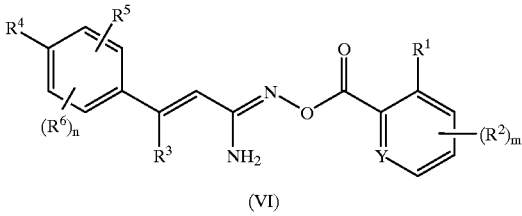

| Ex. No. | R¹ (R²)ₘ Y R³ | R⁵ R⁴ (R⁶)ₙ | Physical constants |
|---|---|---|---|
| VI-12 | F, Cl, H | 4-(4-trifluoromethoxyphenoxy)phenyl | m.p.: oil |
| VI-13 | F, Cl, H | 4-tert-butylphenyl | m.p.: oil |
| VI-14 | Cl, Cl, H | 4-cyclohexylphenyl | m.p.: 155–157° C. | a) ¹H NMR (400 MHz, CDCl₃, δ) in ppm

Preparation of the Starting Compounds

EXAMPLE (XI-1)

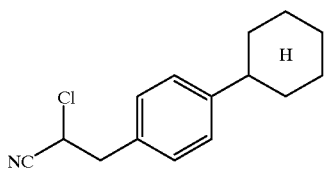

56 ml of 25 percent strength hydrochloric acid and 32.9 g (0.62 mol of acrylonitrile are added to 35.1 g (0.2 mol) of 4-cyclohexyl-aniline in 56 ml of acetone, 15.2 g (0.22 mol) of sodium nitrite in 25 ml of water are then added dropwise at 0° C. to 10° C. with stirring in the course of one hour, the mixture is stirred for a further hour at 0° C. to 10° C., and several portions of copper(II) oxide/copper(I) bromide powder are then added, whereupon a vigorous evolution of nitrogen gas can be observed. After the evolution of gas has ceased, the mixture is stirred for a further 15 hours at room temperature, dichloromethane is then added, the mixture is washed with water, dried over sodium sulfate and concentrated in vacuo, and the crude product which remains is purified over a silica gel column (silica gel 60—Merck, particle size: 0.040 to 0.063 mm) using cyclohexane/ethyl acetate (1:1) as the eluent.

42.2 g (85.2% of theory) of 2-chloro-1-(4-cyclohexyl-phenyl)-propionitrile are obtained as an oil.

¹H-NMR (400 MHz, CDCl₃, δ): 3.25 (2H, —CH₂—); 4.52 (1H, —CHCl—) ppm

The following 3-aryl-2-chloro-propionitriles of Table 11 are obtained analogously and in accordance with the general preparation instructions:

TABLE 11
Examples of 3-aryl-2-chloro-propionitriles of the formula (XI)
(XI)
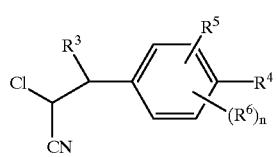
| Ex. No. | $R^3$ | 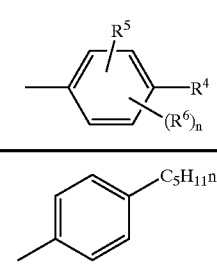 | Physical constants |
|---|---|---|---|
| (XI-2) | H | 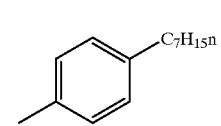 4-$C_5H_{11}$n | 4.53 (1H, —CHCl—); 3.27 (2H, —CH$_2$—)[a)] |
| (XI-3) | H | 4-$C_6H_{13}$n | 4.52 (1H, —CHCl—); 3.27 (2H, —CH$_2$—)[a)] |
| (XI-4) | H | 4-$C_7H_{15}$n | 4.52 (1H, —CHCl—); 3.27 (2H, —CH$_2$—)[a)] |
| (XI-5) | H | 4-$C_{10}H_{21}$n | 4.52 (1H, —CHCl—); 3.27 (2H, —CH$_2$—)[a)] |
| (XI-6) | H | 4-$C_{12}H_{25}$n | 4.52 (1H, —CHCl—); 3.27 (2H, —CH$_2$—)[a)] |
| (XI-7) | H | 4-$C_{14}H_{29}$n | 4.52 (1H, —CHCl—); 3.26 (2H, —CH$_2$—)[a)] |
| (XI-8) | H | 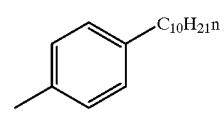 | 4.56 (1H, —CHCl—); 3.30 (2H, —CH$_2$—)[a)] |
| (XI-9) | H | 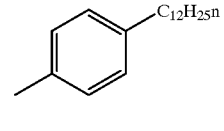 | 4.59 (1H, —CHCl—); 3.31 (2H, —CH$_2$—)[a)] |
| (XI-10) | H | 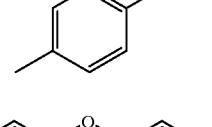 | m.p.: oil |

TABLE 11-continued

Examples of 3-aryl-2-chloro-propionitriles of the formula (XI)

| Ex. No. | R³ | (structure) | Physical constants |
|---|---|---|---|
| (XI-11) | H | 4-(4-tert-butylphenylthio)phenyl | m.p.: oil |
| (XI-12) | H | 4-(4-tert-butylbenzyl)phenyl | m.p.: oil |
| (XI-13) | H | 4'-tert-butyl-biphenyl-4-yl | m.p.: 54–56° C. | a) ¹H NMR (400 MHz, CDCl₃, δ) in ppm

EXAMPLE (X-2)

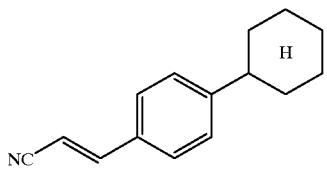

27.1 g (0.176 mol) of diazabicycloundecene in 100 ml of tetrahydrofuran are added dropwise at room temperature with stirring to 40.0 g (0.16 mol) of 2-chloro-1-(4-cyclohexyl-phenyl)-propionitrile in 150 mol of tetrahydrofuran, and, after the addition has ended, the mixture is stirred for 15 hours at room temperature and filtered, the filtrate is concentrated in vacuo, the residue is taken up in ethyl acetate, the mixture is washed in succession using 1N hydrochloric acid and water and dried over sodium sulfate, and the solvent is removed in vacuo. 22.8 g (67.4% of theory) of (E/Z)-4-cyclohexylcinnamonitrile of melting point m.p. 53–54° C. are obtained.

Examples for the preparation of the substituted cinnamonitriles employed as precursor (cf. EP O 318 704 A2; J. A. Claisse et al. J. C. S. Perkin I, pp. 2241–2249).

EXAMPLE (X-1)

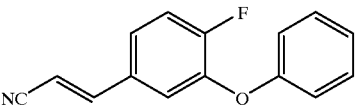

A solution of 26.6 g (0.15 mol) of diethyl cyanomethylphosphonate in 100 ml of tetrahydrofuran is added dropwise to a suspension of 17.7 g (0.315 mol) of pulverulent potassium hydroxide in 300 ml of tetrahydrofuran and 32.4 g (0.15 mol) of 4-fluoro-3-phenoxy-benzaldehyde. The process is slightly exothermic. Stirring of the mixture is subsequently continued for 20 minutes at room temperature, and the solid which separates out is filtered off and washed using tetrahydrofuran. The filtrate is concentrated in vacuo, and the residue which remains is dried. 33.5 g (93.5% of theory) of (E/Z)-4-fluoro-3-phenoxy-cinnamonitrile are obtained.

¹H NMR (400 MHz, CDCl₃, δ): 5.41 (d, 1H, —CH=, $J_{H,H}$=12.0 Hz; Z form); 5.74 (d, 1H, —CH=, $J_{H,H}$=16.5 Hz; E form) in ppm Table 12
Examples of substituted (E/Z-cinnamonitriles by Methods A and B

TABLE 12

Examples of substituted (E/Z-cinnamonitriles by Methods A and B

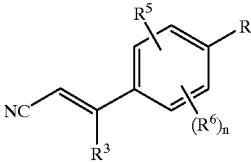

| Ex. No. | R³ | | Physical constants |
|---|---|---|---|
| (X-3) | H | 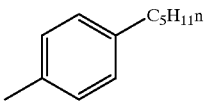 | 5.82; 7.22 E form[a]<br>5.37; 7.08 Z form |
| (X-4) | H | 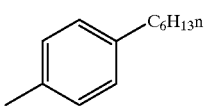 | 5.82; 7.22 E form[a]<br>5.37; 7.08 Z form |
| (X-5) | H | 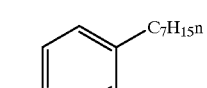 | 5.81; 7.22 E form[a]<br>5.37; 7.09 Z form |
| (X-6) | H | 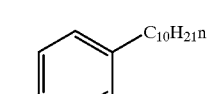 | 5.82; 7.22 E form[a] |
| (X-7) | H | 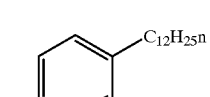 | 5.82; 7.22 E form[a] |
| (X-8) | H | 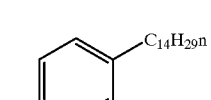 | 5.85; 7.35 E form[a] |
| (X-9) | H | 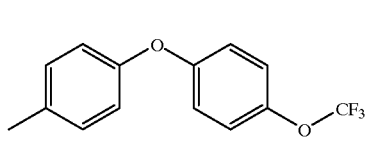 | 5.78; 7.35 E form[a]<br>5.39;   Z form |
| (X-10) | H | 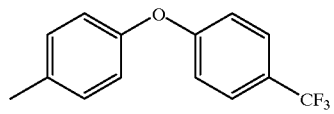 | 6.44; 7.67 E form[b]<br>5.87;   Z form |
| (X-11) | H | 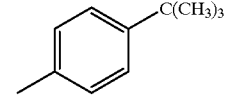 | 5.83;   E form[a]<br>5.38; 7.09 Z form |

TABLE 12-continued

Examples of substituted (E/Z-cinnamonitriles by Methods A and B

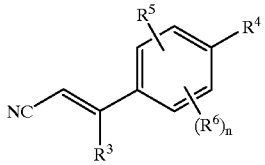

| Ex. No. | R³ | 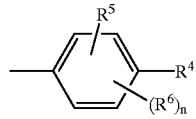 | Physical constants |
|---|---|---|---|
| (X-12) | H | 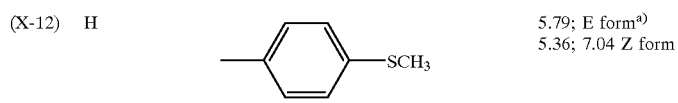 | 5.79; E form[a)]<br>5.36; 7.04 Z form |
| (X-13) | H | 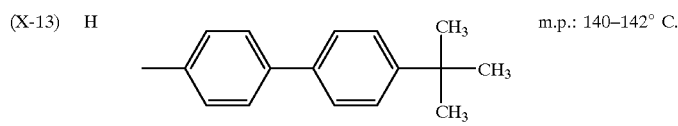 | m.p.: 140–142° C. |
| (X-14) | H | 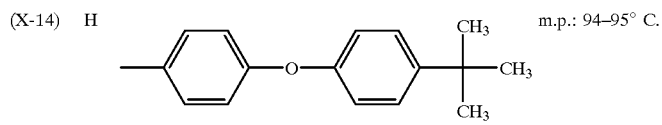 | m.p.: 94–95° C. |

[a)]$^1$H NMR (400 MHz, CDCl$_3$, δ) [b)]$^1$H NMR (400 MHz, DMSO-d$_6$, δ) in ppm; doubletts in each case ($J_{H,H}$ = 16.5 Hz; E form) and ($J_{H,H}$ = 12.0 Hz; Z form) for —Hc=CH—

Example Precursor for Example IX-1

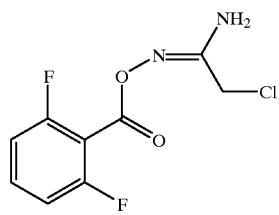

EXAMPLE (IX-1)

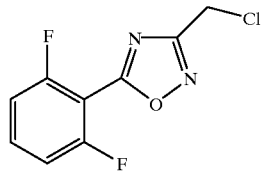

21.4 g (0.2 mol) of chloroacetamide oxime and 19.4 g (0.2 mol) of triethylamine are introduced into 100 ml of 1,4-dioxane, and 34.6 g (0.2 mol) of 2,6-difluoro-benzoyl chloride are added dropwise, with cooling. After stirring has been continued for approximately 2 hours at room temperature, the entire reaction batch is poured into 400 ml of water, and the solid which precipitates is filtered off with suction. After recrystallization from methanol, 15.3 g (32.4% of theory) of O-(2,6-difluorobenzoyl)-chloroacetamide oxime of melting point of 100 to 101° C. are obtained.

8.0 g (0.03 mol) of O-(2,6-difluorobenzoyl)-chloroacetamide oxime are heated in 16 ml of glacial acetic acid until cyclization is complete (approximately 2.5 hours).

The entire reaction mixture is then concentrated in vacuo, and the product is stirred with approximately 400 ml of water and subsequently extracted using methylene chloride. The organic phase is dried over sodium sulfate, and the solvent is distilled off in vacuo. The crude product which remains is chromatographed over a silica gel column (silica gel 60-Merck, particle size: 0.040 to 0.063 mm) using toluene: methanol (9:1) as the eluent. 3.4 g (49.1% of theory) of 3-chloromethyl-5-(2,6-diflurophenyl)-1,2,4-oxadiazole of melting point m.p. 33 to 34° C. are obtained.

EXAMPLE (VIIa-1)

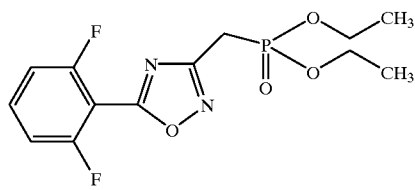

5.1 g (0.022 mol) of 3-chloromethyl-5-(2,6-difluorophenyl)-1,2,4-oxadiazole are stirred with 5.3 ml (0.031 mol) of triethyl phosphite, and the mixture is refluxed for 1 hour. The reaction mixture is subsequently concentrated in vacuo, and the residue which remains is purified over a silica gel column (silica gel 60-Merek, particle size: 0.040 to 0.063 mm) using ethyl acetate as the eluent. 4.7 g (64.3% of theory) of 3-(diethoxyphosphonomethyl)-5-(2,6-difluorophenyl)-1,2,4-oxadiazole of melting point 67 to 69° C. are obtained.

$^1$H NMR (400 MHz, CDCl$_3$, δ): 1.36 (t, 6H, 2×—CH$_3$; $J_{H,H}$=7.0 Hz); 3.48 (d, 2H, —CH$_2$—P; $J_{H,P}$=21.3 Hz); 4.10–4.26 (m, 4H, 2×—O—CH$_2$—); 7.11 (m, 2H, arom. —H); 7.58 (m, 1H, arom. —H) ppm.

$^{31}$P NMR (162 MHz, CDCl$_3$, δ): 20.9 ((Et—O)$_2$P=O) ppm

EI MS m/z (%): 332 (M$^+$, 12)

EXAMPLE A
Tetranychus Test (OP Resistant/spray Treatment)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Beanplants (*Phaseolus vulgaris*) which are severely infested with all stages of the greenhouse red spider mite, or two-spotted spider mite (*Tetranychus urticae*), are sprayed with a preparation of active compound of the desired concentration.

After the specified period of time, the activity in % is determined. 100% means that all the spider mites have been killed; 0% means that none of the spider mites have been killed.

In this test, a degree of destruction of at least 95% is shown, after 7 days, for example by the compounds of Preparation Examples I-1, I-4, I-5, I-8, I-10, I-12 and X-12 at an exemplary active compound concentration of 0.1%.

EXAMPLE B
Phaedon Larvae Test

Solvent: 7 parts by weight of dimethylformamide
Emulsifier 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with mustard beetle larvae (*Phaedon cochlearia*) while the leaves are still moist.

After the specified period of time, the destruction in % is determined. 100% means that all the beetle larvae have been killed; 0% means that none of the beetle larvae have been killed.

In this test, a degree of destruction of 100% is shown, after 7 days, for example by the compounds of Preparation Examples I-12, I-17, XI-8, and XI-9 at an exemplary active compound concentration of 0.1%.

EXAMPLE C
Panonychus Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Plum trees (*Prunus domestica*) approximately 30 cm high which are severely infested with all stages of the fruit tree red spider mite (*Panonychus ulmi*) are sprayed with a preparation of active compound of the desired concentration.

After the specified period of time, the activity in % is determined. 100% means that all the spider mites have been killed; 0% means that none of the spider mites have been killed.

In this test, a degree of destruction of at least 95% is shown, after 7 days, for example by the compounds of Preparation Examples I-1, I-4, I-5, I-8, I-10, and I-12 at an exemplary active compound concentration of 0.1%.

EXAMPLE D
Nephotettix Test

Solvent: 7 parts by weight of dimethylformamide
Emulsifier 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with the green rice leafhopper (*Nephotettix cincticeps*) while the leaves are still moist.

After the specified period of time, the destruction in % is determined. 100% means that all the leaf hoppers have been killed; 0% means that none of the leafhoppers have been killed.

In this test, a degree of destruction of 100% is shown, after 6 days, for example by the compounds of Preparation Examples (XI-8) and (XI-9) at an exemplary active compound concentration of 0.1%.

EXAMPLE E
Plutella Test

Solvent: 7 parts by weight of dimethylformamide
Emulsifier 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, a degree of destruction of 100% is shown, after 7 days, for example by the compounds of Preparation Examples 1–17 and (VIIa-1) at an exemplary active compound concentration of 0.1%.

What is claimed is:

1. A 3-aryl-alkenyl-1,2,4-oxadiazole derivative of the formula (I-a)

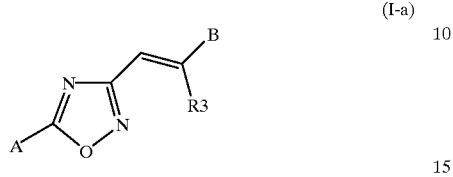

in which

A represents

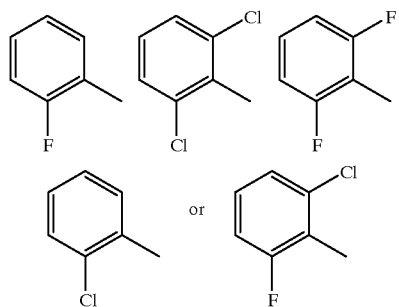

B represents

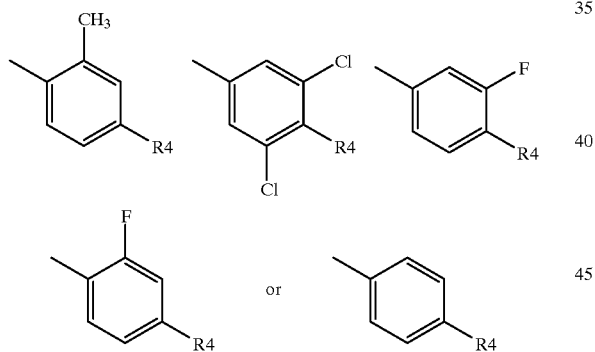

$R^3$ represents hydrogen $R^4$ represents $A_k$—$R^7$ in which

A represents oxygen, sulphur, alkylene, alkyleneoxy or oxyalkylene k represents a number 0 or 1, $R^7$ represents alkyl, halogenoalkyl, optionally substituted cycloalkyl, optionally substituted phenyl or optionally substituted pyridyl provided that B does not represent

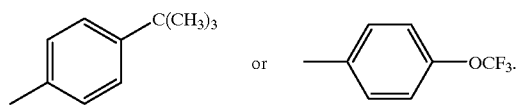

2. 3-aryl-alkenyl-1,2,4-oxadiazole derivative of the formula (I-a) as claimed in claim 1, in which $R^3$ represents hydrogen, $R^4$ represents a group —$A_k$—$R^7$ in which A represents oxygen, sulfur, $C_1$–$C_4$-alkylene, $C_1$–$C_4$-alkyleneoxy, or $C_1$–$C_4$-oxyalkylene, k represents a number 0 or 1 and $R^7$ represents $C_1$–$C_{20}$-alkyl, which is optionally monosubstituted or polysubstituted by fluorine or chlorine, $C_3$–$C_{10}$-cycloalkyl which is optionally monosubstituted to trisubstituted by identical or diffefernt substituents, phenyl which is optionally monsubstituted to pentasubstituted by identical or different substituents, of pyridyl which is optionally monosubstituted to trisubstituted by identical or different substituents, suitable cycloalkyl, phenyl and pyridyl substituents being those mentioned below:

F, Cl, Br, $C_1$–$C_{18}$-alkyl, $C_1$–$C_6$-alkoxy-$C_1$–$C_8$-alkyl, $C_1$–$C_8$-alkoxy which is monosubstitutedd to hexasubstituted by identical or different substituents selected from the group consisting of F, and Cl, $C_1$–$C_2$-alkyl which is monosubstituted to pentasubstituted by identical or different substituents selected from the group consisting of F and Cl, $C_1$–$C_{18}$-alkoxy and —$(OC_2H_4)_{1-3}$—O—$C_1$–$C_6$-alkyl, $C_1$–$C_{12}$-alkylthio, $C_1$–$C_8$-alkylthio which is monosubstituted to hexasubstituted by identical or different substituents selected from the group consisting of F and Cl, 3,4-difluoromethylenedioxo, 3,4-tetrafluoroethylenedioxo, the groups

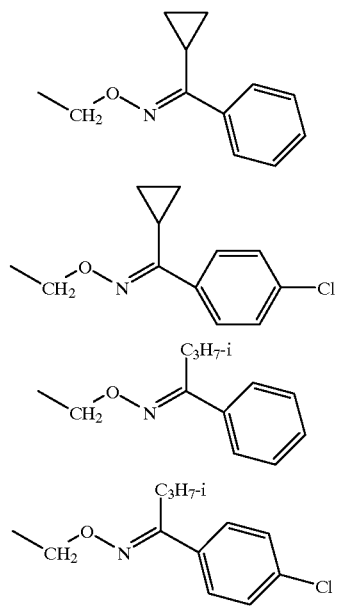

cyclohexyl and cyclohexyloxy, each of which is optionally substituted by $C_1$–$C_4$-alkyl, $C_1$–$C_4$-alkoxy, cyclohexyl or phenyl;

pyridyloxy which is optionally monosubstituted or disubstituted by identical or different substituents selected from the group consisting of F, Cl, and $CF_3$;

phenyl, benzyl, phenoxy, phenylthio, benzyloxy and benzylthio, each of which is optionally monosubstituted or disubstituted by identical or different substituents selected from the group consisting of $C_1$–$C_{12}$-alkyl, F, Cl, Br, $CF_3$, $C_1$–$C_4$-alkoxy, $C_1$–$C_4$-alkoxy which is monosubstituted to hexasubstituted by identical or different substituents selected from the group consisting of F and Cl, $C_1$–$C_4$-alkoxy-$C_1$–$C_4$-alkyl, $C_1$–$C_4$-alkoxyethyleneoxy, $C_1$–$C_4$-alkylthio and $C_1$–$C_4$-alkylthio which is monosubstituted to hexasubstituted by identical or different substituents selected from the group consisting of F and Cl.

3. The compound of the formula

4. The compound of the formula

5. A process for the preparation of 3-aryl-alkenyl-1,2,4-oxadiazole derivatives of the formula (I-a) as claimed in claim 1, which comprises a) reacting amide oxime derivatives of the formula (II)

(II)

in which
$R^3$, $R^4$, $R^5$, $R^6$ and n have the meanings given in claim 1 with carboxylic acid derivatives of the formulae (III), (IV) or (V)

(III)

(IV)

(V)

in which
$R^1$, $R^2$, Y and m have the meanings, in claim 1
R represents alkyl, in particular methyl or ethyl, and
Hal represents halogen,
if appropriate in the presence of a diluent and if appropriate in the presence of a reaction auxiliary,
or b) cyclizing compounds of the formula (VI)

(VI)

in which
Y, $R^1$, $R^2$, $R^3$, $R^4$, $R^5$, $R^6$, m and n have the above-mentioned meanings,
in the presence of a diluent and if appropriate in the presence of a reaction auxiliary,
or c) reacting phosphonium halides of the formula (VII)

(VII)

in which

R¹, R², Y and m have the abovementioned meanings and

Hal represents chlorine, bromine or iodine, or phosphonic esters of the formula (VIIa)

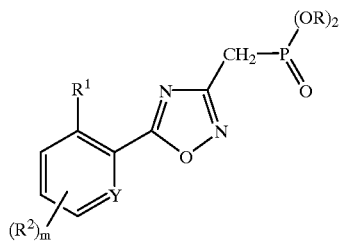

(VIIa)

in which

R¹, R², Y and m have the abovementioned meanings and

R represents alkyl with aldehydes or ketones of the formula (VIII)

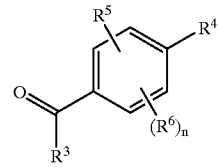

(VIII)

in which

R³, R⁴, R⁵, R⁶ and n have the abovementioned meanings, in the presence of a diluent and if appropriate in the presence of a reaction auxiliary.

6. A pesticide which comprises at least one compound of the formula (I-a) as claimed in claim 1.

7. A method of combating animal pests, wherein compounds of the formula (I-a) as claimed in claim 1 are allowed to act on animal pests and/or their environment.

8. A process for the preparation of pesticides, which comprises mixing compounds of the formula (I-a) as claimed in claim 1 with extenders and/or surfactants.

* * * * *